United States Patent [19]
Borkowski et al.

[11] Patent Number: 5,750,826
[45] Date of Patent: May 12, 1998

[54] BRADYKININ B2 RECEPTOR MODIFIED TRANSGENIC NON-HUMAN ANIMALS

[75] Inventors: Joseph A. Borkowski; Howard Y. Chen; John W. Hess, all of Westfield; Catherine D. Strader, Verona, all of N.J.; Myrna E. Trumbauer, Yardley, Pa.

[73] Assignee: Merck & Co., Inc., Rahway, N.J.

[21] Appl. No.: 759,848

[22] Filed: Dec. 2, 1996

Related U.S. Application Data

[63] Continuation of Ser. No. 281,393, Jul. 27, 1994, abandoned.
[51] Int. Cl.$^6$ .................... A61K 49/00; C12N 15/00; C12N 15/09
[52] U.S. Cl. ..................... 800/2; 435/172.3; 424/9.1
[58] Field of Search ........................ 800/2; 485/172.3; 536/23.1; 435/69.1, 69.6, 320.1, 243; 424/9.1, 9.2

[56] References Cited

PUBLICATIONS

Yang et al. 1992. Theriogenology 38(2): 315–335.
Perkins, Martin N. et al., Antinociceptive activity of the bradykinin B1 and B2 receptor antagonists, des–Arg$^9$, [Leu8]–BK and HOE 140, in two models of persistent hyperalgesia in the rat, Pain, vol. 53, pp. 191–197, 1993.
McEachern, Adrienne E., et al., Expression cloning of a rat B2 bradykinin receptor, Proc. Natl. Acad. Sci. USA, vol. 88, p. 7724–7728, 1991.
Burch and Axelrod, Dissociation of bradykinin–induced prostaglandin formation from phosphatidylinositol turnover in Swiss 3T3 fibroblasts: Evidence for G protein regulation of phospholipase A2.
Strader, Catherine et al., Structural basis of B–adrenergic receptor function, The FASEB Journal, vol. 3, pp. 1825–1832, 1989.
Chartrain, Nicole et al., Molecular Cloning, Structure and Chromosomal Localization of the Human Inducible Nitric Oxide Synthase Gene, The Journal of Biological Chemistry, vol. 269, No. 9, pp. 6765–6772, 1994.
Rinas, Ursula, et al., Characterization of Recombinant Factor XIIIa Produced in Saccharomyces Cerevisiae, Biotechnology, pp. 543–546, 1990.
Perkins & Kelly, Induction of bradykinin B1 receptors in vivo in a model of ultra–violet irradiation–induced thermal hyperalgesia in the rat, Br. J. Pharmacol., vol. 110, pp. 1441–1444, 1993.
Schneck, Kathryn, et al., Bradykinin B1 receptors in rabbit aorta smooth muscle cells in culture, European J. of Pharmacol., vol. 266, pp. 277–282, 1994.
Tropea, Margaret et al., B1 and B2 kinin receptors on cultured rabbit superior mesenteric artery smooth muscle cells: receptor-specific stimulation of inositol phosphate formation and arachidonic acid release by des–arg–bradykinin an dbradykinin, Journal of Pharmacol. and Experimental Therapeutics, vol. 264, No. 2, pp. 930–937, 1993.

Horowitz, Burton et al., Synthesis and Assembly of Functional Mammalian Na, K–ATPase in Yeast, Journal of Biological Chemistry, vol. 265, No. 8, pp. 4189–4192, 1990.
Goldstein & Wall, Activation of Protein Formation and Cell Division by Bradykinin and Des–Arg9–bradykinin, The Journal of Biological Chemistry, vol. 259, No. 14, pp. 9263–9268, 1984.
Slivka and Insel, Phorbol Ester and Neomycin Dissociate Bradykinin Receptor–mediated Arachidonic Acid Release and Polyphosphoinositide Hydrolysis in Madin–Darby Canine Kidney Cells, Journal of Biological Chemistry, vol. 263, No. 29, pp. 14640–14647, 1988.
Phillips, Elsa et al., Expression of Functional Bradykinin Receptors in Xenopus Oocytes, Journal of Neurochemistry, vol. 58, No. 1, pp. 243–249, 1992.
Regoli and Barabe, Pharmacology of Bradykinin and Related Kinins, Pharmacological Reviews, vol. 32, No. 1, pp. 1–46, 1980.
Masu, Yasuo et al., cDNA cloning of bovine substance–K receptor through oocyte expression system, Nature, vol. 329, pp. 836–838, 1987.
Dray and Perkins, Bradykinin and inflammatory pain, J. Neurophysiol., vol. 63, pp. 256–272, 1993.
Couture, R. et al., Peptides and the human colon: an in vitro pharmacological study, Can. J. Physiol. Pharmacol., vol. 59, pp. 957–964 1981.
Wirth, Klaus et al., DesArg9–D–Arg[Hyp3,Thi5,D–Tic7, Oic8]bradykinin (desArg10–[Hoe140]) is a potent bradykinin B1 receptor antagonist, European Journal of Pharmacology, vol. 205, pp. 217–218, 1991.
Regoli, Domenico et al., Conversion of kinins and their antagonists into B1 Receptor activators and blockers in isolated vessels, European Journal of Pharmacology, vol. 127, pp. 219–224, 1986.
Regoli, D. et al., Receptors for bradykinin in rabbit aortae, Can. J. Physiol. Pharmacol., vol. 55, pp. 855–867, 1977.
Regoli, D. et al., De novo formation of vascular receptors for bradykinin 1, Can. J. Physiol. Pharmacol, vol. 56, pp. 674–677, 1978.
Regoli, Domenico et al., Induction of B1–Receptors for kinins in the rabbit by a bacterial lipopolysaccharide, European Journal of Pharmacology, vol. 71, pp. 105–115, 1981.
Farmer, S.G. et al., Induction of vascular smooth muscle bradykinin B1 receptors in vivo during antigen arthritis, Agents and Actions, vol. 34, pp. 191–193, 1993.
Deblois, Denis et al., Effect of glucocorticoids, monokines and growth factors on the spontaneously developing responses of the rabbit isolated aorta to des–Arg9–bradykinin, Br. J. Pharmacol., vol. 93, pp. 969–977, 1988.

(List continued on next page.)

*Primary Examiner*—Brian R. Stanton
*Attorney, Agent, or Firm*—Michael D. Yablonsky; Jack L. Tribble

[57] ABSTRACT

A transgenic non-human animal with alterations in a bradykinin B2 receptor gene is prepared by introduction of a gene encoding an altered bradykinin B2 receptor into a host non-human animal.

6 Claims, 7 Drawing Sheets

OTHER PUBLICATIONS deBlois, Denis et al., Pulse exposure to protein synthesis inhibitors enhances vascular responses to des–Arg9–bradykinin: possible role of interleukin–1, Br. J. Pharmacol. vol. 103, pp. 1057–1066, 1991.

deBlois, Denis et al., Pharmacological modulation of the up–regulated responses to des–Arg9–bradykinin in vivo and in vitro, Immunopharmacology, vol. 17, pp. 187–198, 1989.

Burch, R.M. et al. The Kallikrein–kininogen–kinin system in chronic inflammation, Agents and Actions, vol. 27, 3/4, pp. 258–260, 1989.

Tiffany and Burch, Bradykinin stimulates tumor necrosis factor and interleukin–1 release from macrophages, vol. 247, No. 2, pp. 189–192, 1989.

Proud, David, Kinin formation: Mechanisms and role in inflammatory disorders, Ann. Rev. Immunol., vol. 6: pp. 49–83, 1988.

Rhaleb, N. et al., Receptors for kinins in isolated arterial vessels of dogs, European Journal of Pharmacology, vol. 162, p. 419–427.

Lortie, Mark et al., The role of B1–and B2–kinin receptors in the renal tubular and hemodynamic response to bradykinin, American Physiological Society, vol. 262, pp. R72–R76, 1992.

Powell, Steven J. et al., Human Bradykinin B2 Receptor: Nucleotide Sequence Analysis and Assignment to Chromosome 14, Genomics, vol. 15, pp. 435–438, 1993.

Hess, Fred J. et al., Cloning and Pharmacological Characterization of a Human Bradykinin (BK–2) Receptor, Biochemical and Biophysical Research Communications, vol. 184, No. 1, pp. 260–268, 1992.

Eggerickx, Dominique et al., Molecular Cloning, Functional Expression and Pharmacological Characterization of a Human Bradykinin B2 Receptor Gene, vol. 187, No. 3, pp. 1306–1313, 1992.

Giladi and Spindel, Simple Luminometric Assay to detect Phosphoinositol–Linked Receptor Expression in Xenopus Oocytes, vol. 10, No. 6, pp. 744–747, 1991.

Hock, F.J. et al., Hoe 140 a new potent and long acting bradykinin–anagonist: in vitro studies, J. Pharmacol., vol. 102, pp. 769–773, 1991.

Sandberg, Kathryn et al., Calcium mobilization by angiotensin II and nerotransmitter receptors expressed in Xenopus laevis oocytes, FEBS Letters, vol. 241, No. 1,2 pp. 177–180, 1988.

Huang, Ruey–Ruey C., et al., Identification of Allosteric Antagonists of Receptor–Guanine Nucleotide–Binding Protein Interactions, Molecular Pharmacology, vol. 37, pp. 304–310, 1989.

Kitts, Paul A. et al., Linearization of baculovirus DNA enhances the recovery of recombinant virus expression vectors, Nucleic Acids Research, vol. 18, No. 19, 1990.

Hess, Fred J. et al., Differential Pharmacology of Cloned Human and Mouse B2 Bradykinin Receptors, Molecular Pharmacology, vol. 45, pp. 1–8, 1993.

H. Baribault et al., Embryoic Stem Cell Culture and Gene Targeting in Transgenic Mice, Mol. Biol. 6: 481–492 (1989).

A. Bradley, Production and Analysis of Chimaeric Mice, IRL Press, 113–151 (1987).

A. Bradley et al., Modifying the Mouse: Design and Desire, Bio/Technology 10: 534–539 (1992).

A. Bradley et al. Formation of Germ–line Chimaeras From Embryo–derived Teratocarcinoma Cell Lines, Nature 309: 255–256 (1984).

C.A. Brenner et al., Genes for Extracellular Matrix–degrading Metalloproteinases and Their Inhibitor, TIMP, are Expressed During Early Mammalian Development, Genes & Development 3: 848–859 (1989).

M.R. Capecchi, Altering the Genome by Homologous Recombination, Science 244: 1288–1292 (1989).

M.R. Capecchi, The New Mouse Genetics: Altering the Genome by Gene Targeting, Trends in Genetics 5: 70–76 (1989).

G.A. Evans et al., High Efficiency Vectors for Cosmid Microcloning and Genomic Analysis, Gene 79: 9–20 (1989).

M.J. Evans et al., Establishment in Culture of Pluripotential Cells from Mouse Embroys, Nature 292: 154–156 (1981).

M.A. Frohman et al., Cut, Paste and Save: new Approaches to Altering Specific Genes in Mice, Cell 56: 145–147 (1989).

A. Gossler et al., Transgenesis By Means of Blastocyst––Derived Embryonic Stem Cell Lines, Proc. Natl. Acad. Sci., USA 83: 9065–9069 (1986).

R. Jaenisch, Transgenic Animals, Science 240: 1468–1474 (1988).

H.S. Kim et al., Problems Encountered in Detecting a Targeted Gene by the Polymerase Chain Reaction, Gene 103: 227–233 (1991).

F.L. Lin et al., Recombination in Mouse L Cells Between DNA Introduced Into Cells and Homologous Chromosomal Sequences, Proc., Natl. Acad. Sci. USA 82: 1391–1395 (1992).

S.L. Mansoure et al., Disruption of the Proto–Oncogene Int–2 in Mouse Embryo–Derived Stem Cells: a General Strategy for Targeting Muttions to Non–Selectable Genes, Nature 336: 348–352 (1988).

J.S. Mudgett et al., Isolation of the Functional Human Excision Repair Gene ERCC5 by Intercosmid Recombination Genomics 8: 623–633 (1990).

H.T. Riele et al., Highly Effective Gene Targeting in Embryonic Stem Cells Through Homologous Recombination with Isogenic DNA Constructs, Proc. Natl. Acad. Sci. USA 89: 5128–5132 (1992).

E.J. Robertson, Embryo–Derived Stem Cells Lines, IRL Press, 71–112 (1987).

E. Robertson et al., Germ–Line Transmission of Genes Introduced into Cultured Pluripotential Cells by Retroviral Vector, Nature 322: 445–448 (1986).

J.M. Sedivy et al., Positive Genetic Selection for Gene Disruption in Mammalian Cells by Homologous Recombination, Proc. Natl. Acad. Sci. USA 86: 227–231 (1989).

K.R. Thomas et al., High Frequency Targeting of Genes to Specific Sites in the Mammalian Genome, Cell 44: 419–428.

K.R. Thomas et al., Site–Directed Mutagenesis by Gene Targeting in Mouse Embryo–Derived Cells, Cell 51: 503–512 (1987).

E.F. Wagner, on Transferring Genes into Stem Cells and Mice, the EMBO Journal 9: 3025–3032 (1990).

O. Smithies et al. Insertion of DNA Sequences into the Human Chromosomal b–Globin Locus by Homologous Recombination, Nature 317: 230–234 (1985).

BRADYKININ B2 RECEPTOR MODIFIED TRANSGENIC NON-HUMAN ANIMALS

This application is a continuation of application Ser. No. 08/281,393, filed Jul. 27, 1994, now abandoned.

FIELD OF THE INVENTION

The present invention relates to transgenic nonhuman animals wherein a bradykinin B2 receptor gene is altered.

BACKGROUND OF THE INVENTION

Bradykinin is a hormonal nonapeptide which mediates pain, vascular permeability, inflammation, gastrointestinal function, and smooth muscle tone in vascular and other tissues. Bradykinin (BK) is one of the key mediators of the body's response to trauma and injury. BK levels are generally low until a traumatic event triggers a cascade of biochemical reactions and a rise in the concentration of BK by proteolytic generation. High molecular weight precursors, the kininogens, are found in blood and tissue. This cascade is initiated by the activation of the Hageman factor which also initiates fibrinolysis and coagulation.

Receptors for BK exist in the nervous system, epithelia, smooth muscle and fibroblasts. In each tissue type BK triggers specific responses including neurotransmitter release, muscle contraction, fluid secretion by epithelia, and the stimulation of cell growth. It can also act as a neurotransmitter.

The initial interaction for biological response occurs at a BK receptor site on a cell. Specific BK antagonists have been developed [Vavrek, Peptides, 6, 161–165 (1995)]. Their potential use includes use as anti-nociceptive and anti-inflammatory agents. Bradykinin activates neurons and produces neurotransmitter release. It also stimulates the production of a number of bioactive intermediates including inositol triphosphate (Ins-1,4,5-$P_3$) and diacylglycerol (DAG) and arachidonic acid(AA) and its cyclooxygenase and lipooxygenase products. These substances cause cellular levels of cAMP, cGMP, and $Ca^{2+}$ to increase. BK also activates phospholipase C and $A_2$. In neurons, the most important points of action for the substances released by BK stimulation are ion channels [Miller, R.J., Trends Neurosci., 10, 226–229 (1987)].

Bradykinin released during tissue damage causes vasodilation, increased vascular permeability, altered gut motility and pain. Specific bradykinin receptors exist in intestinal mucosa and muscle. Bradykinin and analogues stimulate Cl secretion in the gut. Specific BK receptor binding sites occur in the mucosa and in muscle. BK has a contractile effect in muscle [Manning et al., Nature, 299, 256–259 (1982)].

Addition of nanomolar concentrations of BK to the serosal surface of the mucosal layer of the guinea pig ileum rapidly increased transepithelial potential difference (p.d.) and the short circuit current ($I_{SC}$). This suggests localization of BK receptors at the serosal surface of the villus and crypt epithelium. The increase in Isc is thought to be due to stimulation of anion secretion (Cl out of the cell produces a larger potential difference) [Manning et al., Nature, 299, 256–259 (1982).

Bradykinin could open calcium channels as indicated by the inhibitory effects of $Ca^{2+}$ channel blockers. Calcium may be involved in regulating BK receptor binding. See Innis et al., Proc. Natn. Acad. Sci., 2630–2634 (1981). BK also stimulates sodium intake and DNA synthesis. Owen et al., Cell, 32, 979–985 (1983)].

Excessive kinin activity may play some role in carcinoid syndrome and in inflammatory bowel disease. Patients with ulcerative colitis have abnormally high levels of active kallikrein, the kinin-releasing enzyme and plasma and tissue levels of peptidiyl dipeptidase which degrades kinins are depressed in patients with regional enteritis [Manning et al., Nature, 299, 256–259 (1982)].

Autoradiographic studies localize BK receptor binding sites to the substantia gelatinosa, dorsal root, and a subset of small cells in both the dorsal root and trigeminal ganglia of the guinea pig. Binding was also observed over myocardial/coronary visceral afferent fibers. The localization of BK receptors to nociceptive pathways supports a role for BK in pain mediation. Several BK antagonists block BK induced acute vascular pain in the rat. BK antagonists also relieve BK and urate induced hyperalgesia in the rat paw. These results indicate that BK is a physiologic mediator of pain and that BK antagonists have analgesic activity in both acute and chronic pain models. The BK receptor involved in vascular pain may be different from the receptor involved in cutaneous hyperalgesia [Steranka et al., Proc. Natl. Acad. Sci. USA., 85, 3245–3249 (1988)].

BK receptors have been classified as two major subtypes-$B_1$ and $B_2$. The BK metabolite des-Arg-bradykinin is a $B_1$ receptor agonist which has higher potency than BK but it is inactive at $B_2$ receptors [Steranka et al., Proc. Natl. Acad. Sci. USA., 85, 3245–3249 (1988)1. BK also binds to G protein-coupled receptors that activate phospholipase C or phospholipase $A_2$ and increases synthesis of inositol triphosphate or arachidonic acid [Olsen et al., J. Bio. Chem. 263, 18030–18035 (1988)]. G-proteins are a family of membrane proteins that become activated only after binding guanosine triphosphate (GTP). Activated G-proteins in turn activate an amplifier enzyme on the inner face of a membrane; the enzyme then converts precursor molecules into second messengers. For example, an external signal molecule (bradykinin) may bind to its cell-surface receptor (B2) and induce a conformational change in the receptor. This change is transmitted through the cell membrane to a G-protein, making it able to bind to GTP. Binding of GTP causes another confoimational change in the G-protein that enables it to activate adenylate cyclase (amplifier enzyme) to initiate formation of cAMP(second messenger).

In Swiss 3T3 fibroblasts, BK stimulated phospholipase C mediated InsP formation and PGE-2 synthesis. G proteins were implicated in the mediation of the effects of bradykinin suggesting that the receptor is bound to a G protein which interacts with the particular enzyme [Burch et al., Proc. Natl. Aca. Sci. USA, 84, 6374–6377 (1987)]. Two different G-proteins mediate neuropeptide Y and bradykinin stimulated phospholipid breakdown in cultured rat sensory neurons [Perney et al., J Biol. Chem., 264, 7371–7327 (1991)].

It is known that there is a large degree of heterogeneity within the muscarinic, adrenergic, and serotonergic class of receptors. Furthermore, "[s]imple classification of subtypes of BK receptors cannot fully account for the properties of these receptors on cells from a variety of tissues." [Mahan et al., Mol. Pharmacol., 37, 785–789 (1990)].

Bradykinin induced increases in InsP formation through the activation of phosphatidylinositol-specific phospholipase C and subsequent mobilization of intracellular $Ca^{2+}$ and direct activation of phospholipase $A_2$, which causes the release of arachidonate and subsequent synthesis of prostaglandin $E_2$ have been found to exist in Swiss albino mouse 3T3 cells and BALBc (SV-T2) mouse 3T3 cells and involve receptors coupled to pertussis 0 toxin-insensitive G proteins.

These receptors belong to the $B_2$ subtype [Mahan et al., *Mol. Pharmacol.*, 37, 785–789 (1990)].

The effect of bradykinin on the neuroeffector junction of the isolated rat vas deferens has been studied [Llona et al., *J. Pharmacol. Exp. Ther.*, 241, 608–614 (1987)]. BK potentiated the magnitude of the muscular response to the electrically driven twitches and contracted the smooth muscle generating an increased muscle tone. The former action is referred to as the neurogenic or presynaptic effect and the latter is called the musculotropic or postjunctional action. The rat vas deferens contains bradykinin receptors on the nerve endings and on the smooth muscle membrane. The structural prerequisites for the activation of these receptor sites appear to be slightly different. Their results support the existence of $B_2$ receptors. des-$Arg^9$-BK and des-$Arg^9$-[$Leu^8$]-BK are inactive in causing either pre- or postsynaptic BK like responses and incubation of des-$Arg^9$-[$Leu^8$]-BK at high concentrations failed to antagonize BK responses in the vas deferens. This peptide is a known $B_1$ antagonist. The authors suggest that there are several classes of B2 receptors [Llona et al., *J. Pharmacol. Exp. Ther.*, 241, 613 (1997); see also Brass et al., *Br. J. Pharmacol.*, 94, 3–5 (1988)].

As indicated, BK mediates vasodilation, pain and smooth muscle contraction in a number of tissues. Many of these biological actions may result from the release of arachidonic acid and its metabolites. The major metabolite in Swiss 3T3 cells (fibroblasts) is $PGE_2$ which induces smooth muscle contraction, mitogenesis, an increase in intracellular free calcium and stimulates adenylate cyclase(to produce cAMP). BK activates phospholipases which control intracellular arachidonate [Conklin et al., *J. Pharmacol. Exp. Ther.*, 244, 646–649 (1988)].

Phospholipases are considered to be the rate limiting enzymes in receptor mediated arachidonate release. BK activates $PLA_2$, a phospholipase which cleaves arachidonic acid directly from the parent phospholipid. In contrast, BK in CPAE cells (bovine pulmonary artery endothelial cells) stimulates activity of a phosphatidylcholine-specific PLC which provides arachidonate substrate for $PGI_2$ synthesis. The authors conclude that the BK receptors are pharmacologically distinct and that more BK subtypes exist beyond $BK_1$ and $BK_2$ [Conklin et al., *J. Pharmacol. Exp. Ther.*, 244, 646–649 (1988)].

To further clarify the role of bradykinin, kinins are released in response to tissue injury and activate sensory pain fibers, contract venous smooth muscle and stimulate prostacyclin ($PGI_2$) synthesis and endothelium derived relaxing factor (EDRF). Blood flow to the damaged area and vascular permeability increase to cause inflammation [Plevin et al., *Trends Pharmacol. Sci.*, 9, 387–389 (1988)]. Multiple $B_2$ BK receptors in mammalian tissues are present. The tissues include guinea-pig ileum, vas deferens prejunctional, N1E-1 15 P1 response(neuronal cell line), Rat uterus, and guinea-pig trachea (endothelial cells-BK linked to second messenger and coupled to a G-protein).

Because of the potential molecular heterogeneity of bradykinin receptors in cells and discrepancies in their pharmacological classification, there is a need to elucidate and fully characterize a homogeneous human bradykinin receptor and to express this receptor to measure antagonist or agonist response or interaction.

It is known that cDNAs for a number of receptors of the G protein-coupled superfamily have been cloned. These include, for example, a beta-adrenergic receptor, a substance P receptor, and a neurotensin receptor [Strader et al., *Nature* 321, 75–79 (1986); Yokata et al., *J. Biol. Chem.* 264, 17649–17652 (1989); Tanaka et al., *Neuron* 4, 847–854 (1990)].

The precise roles of bradykinin B2 receptors in normal tissue development and maintenance, as well as in embryonal and fetal development, are not known at this time. Due to the putative biological importance of bradykinin B2 receptors in pain and inflammation, the bradykinin B2 receptor (BK2) gene is an important target for embryonic stem (ES) cell manipulation.

The generation of bradykinin B2 receptor deficient transgenic mice would aid in defining the normal role(s) of the bradykinin B2 receptor, and allow an animal model of BK2 deficiency to be used in the design and assessment of chemical approaches to inhibiting BK2 activity. Such BK2 modified transgenic mice can also be used as a source of cells for cell culture.

DETAILED DESCRIPTION OF THE INVENTION

Figure 1:
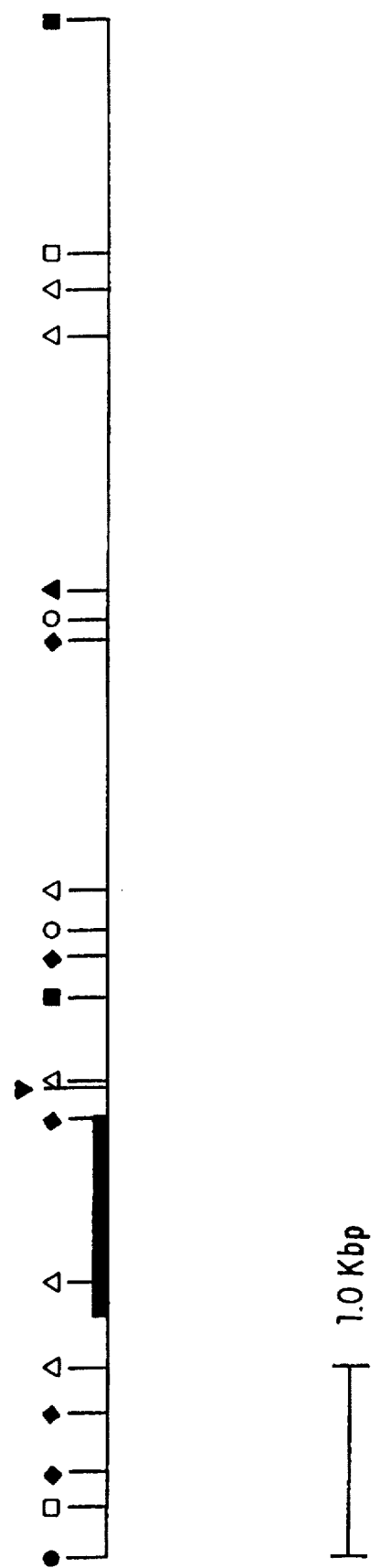
FIG. 1 is a genomic map of the mouse bradykinin B2 gene contained on the murine genomic clone. The restriction sites include Dra I(l), BamiH I (q), Pst I (u), Bgl II (q), Nhe I (n), EcoR I (m), Hind III (s), and Sph I (t). The heavy line indicates the position of the mouse B2 receptor coding sequence.

The present invention utilizes a cloned DNA encoding a human B2 bradykinin receptor protein and describes the cloning and expression of a human bradykinin B2 receptor, as well as the isolation and characterization of the mouse B2 gene. Transgenic animals are generated which have altered the bradykinin B2 receptor gene. The alterations to the naturally occurring gene are modifications, deletions and substitutions. Modifications and deletions render the naturally occurring gene nnonfunctional, producing a "knock out" animal. Substitution of the naturally occurring gene for a gene from a second species results in an animal which produces the receptor of the second species. Substitution of the naturally occurring gene for a gene having a mutation results in an animal which produces the mutated receptor. A transgenic mouse carrying the human B2 receptor is generated by direct replacement of the mouse B2 gene with the human gene. These transgenic animals are critical for drug antagonist studies on animal models for human diseases, and for eventual treatment of disorders or diseases associated with bradykinin elicited responses. Transgenic B2 receptor animals are useful in characterizing the in vivo activity of modulators of human B2 receptor activity. A transgenic animal carrying a "knockout" of the B2 receptor is useful for the establishment of a nonhuman model for diseases involving B2 receptors, and to distinguish between the activities of the different bradykinin receptors in an in vivo system.

The construction of a transgenic mouse in which the human B2 cDNA replaces and disrupts the mouse B2 gene is permitted by the isolation of the mouse genomic B2 gene, the sequence of which is as follows: (SEQ.ID.NO.:1)

```
AAAATGGACTTGAGATGGGTCACTACTCCAGCTTTGTCTGCTTT
GTTCTCCCCAGTCTGGAGGTTTTTAAAAAAATCTCCTTTGGGCCCA
ATCCAGGATTCCTGATGATGGTGATGGAGGTGAGGGTGGTGAG
GGTGGTGATGGTGGTGATGGTGGTGATGGTGGTGATGGTGCTGT
TGATAGTGATGATGATGGTGGTAAGGGAGGAGGGGATGCTGGGT
CTGTGCCCTCCTGAAATCACCACCTACCCAGGACTCATCACAGA
GGAGTCCATGACTGTTAAGAGAAAAACAAGCTCCTTATCCACAC
AGGAGCTACAGGGGCTCTAGATACCTCAGGATCCAAACCATGTC
ACCATGAGTCACAGGCCCCGGCCTGGCTCTAGGGTAGCGCCAGC
CCAGCAGACACTCCGGGGCTCTTCCTGAGAAACCTCAGGATGCT
GAGCAGAGCCTTCTCATCATTCTGCCTAGTGCCTCCTTTCCCCTG
CCCCGCAGTGGAAGGGTCCTCCCATCCCCCACTCTGCAGGTGAC
TAGTCACACGTGCCCTGGGTGTGCTTTAGGCTTTTTAGTGCATCT
TTATAATCATGTTTCGATATTATTCCCATCTTTACTGGTTAGGGG
TCCAAAAACATTAAGCAACTTACCAAGGCCAAACGGTGACCAG
GACTCGGCCCCAGGGGACCAAGCCAAAGTCTCGCCTTTCCTCTT
TCCAGGCAACCTTGGCTCACCTTCTGTGCTTTGCTGCCAGTGGGC
ACAGGCACAAGGTTCTCCCTCTGCTAGAAGACACAGATTGTCAT
GGAGGTGGCTGTGCTCTGGGGGGCCAGACTGCAGTCTCTCCACC
TGGCATGGCATCGCTGATCTGGTCTAATTTATGGCTCACCTGTG
ACCCCACTCTGAGGAGCTGATGGGTCACGGTCCACAGGGGAGA
GGCATGAGAAGGCAGCGAGCACATCTCATAGTGGAGGCTTCAA
AGGGCTCCAGGTGTGGCATTCACGACCATTGGAGTAGCCAGGG
AAGGATTCTTACAGAGTTCAGACCAAGAAAATATCATGTCCCTTT
GGTCCCAGGAAGATCTCTCAAAGGACTGGAGAGTCCAAGTCCC
CTAGTGCTGTCCACAGACCGGAGTCCCACCACCTCCCCACACCC
CACTGCCGCCGGGAGTCATCAGCTGAACAATAGACTTTCTGGTC
CACCTGTCCTGTGCTCCTCCCTGGCCCTCCACCTCCTCCTTCTGC
TATCCCGTTTTCTCTTCCCCTCCCCTCCCCCTCCTTGTGACCTGAG
GATACGACTGTCTCTTCTCTACTTTCTTTCAGCATCGAAATGTTC
AACGTCACCACACAAGTCCTCGGGTCTGCTCTTAACGGGACCCT
TTCGAAGGACAACTGCCCAGACACCGAGTGGTGGAGTTGGCTC
```

```
AATGCCATCCAGGCCCCCTTCCTCTGGGTCCTCTTCCTGCTGGCC
GCACTGGAGAACCTCTtbGTCCTCAGCGTGTTCTTCCTGCACAA
AAACAGCTGCACTGTGGCCGAGATCTACCTGGGCAACCTGGCA
GCGGCGGACCTCATCCTGGCCTGCGGGTTACCTTTCTGGGCCAT
CACCATCGCCAATAACTTTGACTGGGTGTTTGGAGAGGTGTTGT
GCCGGGTGGTGAACACCATGATCTACATGAACCTGTACAGCAGC
ATCTGCTTCCTGATGCTCGTGAGTATCGACCGCTACCTGGCGCT
GGTGAAGACCATGTCCATGGGCCGGATGCGCGGGGTGCGCTGG
GCCAAACTCTACAGCCTGGTGATCTGGGGCTGTACACTGCTTCT
GAGTTCACCCATGTTGGTGTTCAGGACCATGAGGGAATACAGCG
AAGAGGGCCACAATGTCACCGCCTGCGTCATCGTCTACCCGTCC
CGTTCCTGGGAGGTGTTCACCAACGTGCTGCTGAACCTGGTGGG
TTTCCTCCTGCCCCTGAGCGTCATCACCTTCTGCACGGTGCGCAT
CTTGCAGGTGCTGAGGAACAACGAGATGAAGAAGTTCAAGGAG
GTCCAGACGGAGAGGAAGGCCACCGTGCTAGTGCTGGCCGTCC
TGGGGCTCTTTGTGCTGTGTTGGGTGCCTTTCCAGATCAGCACCT
TCCTGGACACGCTGCTGCGCCTCGGCGTGCTGTCCGGATGCTGG
GACGAGCACGCCGTAGACGTCATCACGCAGATCAGTTCCTACGT
GGCCTACAGCAACAGCGGCCTCAACCCACTGGTGTACGTGATCG
TGGGCAAGCGCTTCCGGAAGAAGTCCCGAGAGGTGTACCGGGT
GCTGTGCCAGAAAGGAGGCTGCATGGGAGAACCCGTCCAGATG
GAGAACTCCATGGGGACTTTGAGAACCTCGATCTCCGTGGAACG
GCAGATCCACAAGCTGCAGGACTGGGCAGGGAAGAAACAGTGA
ACAGAAGCCACCAGGCAGGACTACTGCCAAGTGTGTGAGGATT
GGTGGGACCGGAGCTCCTCAGCCTGGGTTCAGAAGGAGCTTGA
AGCATCCTAGGCAGCCCCAGGGAATCAGGCAGGTGACTCCAGC
CCTGTCTCATGGCATAAGCATGCTGTGGGGAATGGGTACCCTGG
GGCACAGCAGGGTCATTCTTACTGACTGACGCTCTAATTCTCCA
TGAGTGGAGGGGTCATGGGTATGGGTGGGAGTGACAGAGCTTC
CTTCCCTTTTGGGGAAGGACAGATCTCCTGCCAGCTTTGGCCCT
GTGGCTACATGCACAGTAGGCATGGCCGCCTCATTTCCCAGTTT
CAAGGGTATAAGATTTATTGGTCTTCTGAAGGTTAAATTCTATG
GTAAGAGCCCAGGGACTGGGTTCTGTGGCTCCTTTCACCTGTAG
ACAAGGTGGACAGCACAAAAGAAGAGCCCCAAAGCATTTATG
GAGCACTTGTTGAATACACACCGTTATACACTGAGGGCAAGAG
GAAAGAACTGCATAGTTTAATGTCTTATAGGAGCCCTGACATTA
GCGGAGAATACCGAGAAGGCTGCTGCTGGTGTGCCAAAGCAAG
GAACTGTGGGAGACGGGAGAGTACAGGGCCCAGGCTAGCCAGT
AACCCCGAACACGGTAGCCTCATCCCTGCCTCTGCTTCTTCGGTT
GTAATCTGAGGGTGTCCTGGGCTTTGAAAGTGGGGTGTTATATG
GCTGTGAGGCATTGTGACCCACACCACCACATGCAGACGCATTG
GGACTCTTGGCACAGAGAAAGCCACTCAGGCTGAAGAGCTACT
CTGTGGGGACACTTAGTATTGGAAGGCCCAGTACCTGCCTGCAG
TGTCTGCGGCCCTCAGTCCCCTCTATCTTTCCCTCCTAGTATTTC
ACCCCTATGCACACAAAAGCACAAAGCATTTGCTCCACAGGAAG
GGCAAGGGCGGGAGACAGCGAGTGTTTGTTTTGCAGGGAAACA
AAGAAAAAGGAATTCATCGATGATATCAGATCTGCCGGTCTCCC
TATAGTGAGTCGTATTAATTTCGATAAGCCAGGTTAACTGCATT
AATGAATCGGCCAACGCGCGGGAGAGGCGGTTTGCGTATTGG
GCGCTCTTCCGCTTCCTCGCTCACTGACTCGCTGCGCTCGGTCGT
TCGGCTGCGGCAGCGTATCAGCTCACTCAAGCGGTAATACGTAT
CACAGAATCAGGGATACGCAGGAAGACATGTGAGAAAGGC.
```

The mouse genomic B2 gene is isolated using the human B2 cDNA. The cDNA sequence encoding the human bradykinin B2 receptor is as follows: (SEQ.ID.NO.: 2)

```
CTCCGAGGAGGGGTGGGGACGGTCCTGACGGTGGGGACATCAGG
CTGCCCCGCAGTACCAGGGAGCGACTTGAAGTGCCCATGCCGCTT
GCTCCGGGAGAAGCCCAGGTGTGGCCTCACTCACATCCCACTCTC
AGTCCAAATGTTCTCTCCCTGGAAGATATCAATGTTTCTGTCTGTT
CGTGAGGACTCCGTGCCCACCACGGCCTCTTTCAGCGCCGACATG
CTCAATGTCACCTTGCAAGGGCCCACTCTTAACGGGACCTTTGCCC
AGAGCAAATGCCCCCAAGTGGAGTGGCTGGGCTGGCTCAACACCA
TCCAGCCCCCCTTCCTCTGGGTGCTGTTCGTGCTGGCCACCCTAGA
GAACATCTTTGTCCTCAGCGTCTTCTGCCTGCACAAGAGCAGCTGC
ACGGTGGCAGAGATCTACCTGGGGAACCTGGCCGCAGCAGACCTG
ATCCTGGCCTGCGGGCTGCCCTTCTGGGCCATCACCATCTCCAACA
ACTTCGACTGGCTCTTTGGGGAGACGCTCTGCCGCGTGGTGAATG
CCATTATCTCCATGAACCTGTACAGCAGCATCTGTTTCCTGATGCT
GGTGAGCATCGACCGCTACCTGGCCCTGGTGAAAACCATGTCCAT
GGGCCGGATGCGCGGCGTGCGCTGGGCCAAGCTCTACAGCTTGGT
GATCTGGGGGTGTACGCTGCTCCTGAGCTCACCCATGCTGGTGTTC
CGGACCATGAAGGAGTACAGCGATGAGGGCCACAACGTCACCGC
```

-continued

```
TTGTGTCATCAGCTACCCATCCCTCATCTGGGAAGTGTTCACCAAC
ATGCTCCTGAATGTCGTGGGCTTCCTGCTGCCCCTGAGTGTCATCA
CCTTCTGCACGATGCAGATCATGCAGGTGCTGCGGAACAACGAGA
TGCAGAAGTTCAAGGAGATCCAGACGGAGAGGAGGGCCACGGTG
CTAGTCCTGGTTGTGCTGCTGCTATTCATCATCTGCTGGCTGCCCTT
CCAGATCAGCACCTTCCTGGATACGCTGCATCGCCTCGGCATCCTC
TCCAGCTGCCAGGACGAGCGCATCATCGATGTAATCACACAGATC
GCCTCCTTCATGCCTACAGCAACAGCTGCCTCAACCCACTGGTGT
ACGTGATCGTGGGCAAGCGCTTCCGAAAGAAGTCTTGGGAGGTGT
ACCAGGGAGTGTGCCAGAAAGGGGGCTGCAGGTCAGAACCCATT
CAGATGGAGAACTCCATGGGCACACTGCGGACCTCCATCTCCGTG
GAACGCCAGATTCACAAACTGCAGGACTGGGCAGGGAGCAGACA
GTGAGCAAACGCCAGCAGGGCTGCTGTGAATTTGTGTAAGGATTG
AGGGACAGTTGCTTTTCAGG.
```

The human B2 bradykinin receptor is cloned from the lung fibroblast cell line CCD-16Lu. The human cDNA clone (SEQ ID NO: 2) encodes a 364 amino acid protein that has the characteristics of a seven transmembrane domain G-protein coupled receptor. The predicted amino acid sequence of the human B2 receptor is approximately twenty percent different than the protein isolated from the smooth muscle rat B2 receptor (81 % homologous) [McEachern et al., Proc. Natl. Acad. Sci. USA 88, 7726 (1991)]. Transfection of the human B2 receptor cDNA into COS-7 cells results in the expression of high levels of specific BK binding sites. Saturation binding analysis indicates that the human B2 receptor expressed in COS-7 cells binds BK with a $K_D$ of 0.13 nM. Pharmacological characterization of the expressed BK receptor cells demonstrates and is consistent with a cDNA encoding for a B2 receptor subtype.

A transgenic mouse carrying the human B2 receptor gene is generated by direct replacement of the mouse B2 receptor gene with the human B2 receptor gene by homologous recombination. The transgenic mouse carrying the human B2 gene is useful in characterizing the in vivo efficacy of antagonists of the human B2 gene isolated from in vitro studies.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered bradykinin B2 gene generally should not fully encode the same bradykinin B2 as native to the host animal, and its expression product should be altered to a minor or great degree, or absent altogether. However, it is conceivable that a more modestly modified bradykinin B2 gene will fall within the compass of the present invention if it is a specific alteration.

The genes used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro (M. J. Evans et al., Nature 292: 154–156 (1981); M. 0. Bradley et al., Nature 309: 255–258 (1984); Gossler et al. Proc. Natl. Acad. Sci. USA 83: 9065–9069 (1986); Robertson et al., Nature 322, 445–448 (1986); S. A. Wood et al. Proc. Natl. Acad. Sci. USA 90: 4582–4584 (1993)). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468–1474 (1988)).

Since B2 is an independent component of a complex mechanism, the receptors, including that encoded by B2, must be examined both individually and as a group if their contribution to the mechanisms of pain and inflammation are to be understood. One approach to the problem of determining the contributions of individual genes and their expression products is to use isolated B2 genes to selectively inactivate the native wild-type gene in totipotent ES cells (such as those described above) and then generate transgenic mice. The use of gene-targeted ES cells in the generation of gene-targeted transgenic mice was described 1987 (Thomas et al., Cell 51:503–512, (1987)) and is reviewed elsewhere (Frohman et al., Cell 56:145–147 (1989); Capecchi, Trends in Genet. 5:70–76 (1989); Baribault et al., Mol. Biol. Med. 6:481–492, (1989); Wagner, EMBO J. 9: 3025–3032 (1990); 20 Bradley et al., Bio/Technology 10: 534–539 (1992)).

Techniques are available to inactivate or alter any genetic region to any mutation desired by using targeted homologous recombination to insert specific changes into chromosomal alleles. However, in comparison with homologous extrachromosomal recombination, which occurs at frequencies approaching 100% homologous plasmid-chromosome recombination was originally reported to only be detected at frequencies between $10^{-6}$ and $10^{-3}$ (Lin et al., Proc. Natl.

Acad. Sci. USA 82:1391–1395 (1985); Smithies et al., Nature 317: 230–234 (1985); Thomas et al., Cell 44:419–428, (1986); Song et al., Proc. Natl. Acad. Sci. USA 84:6820–6824 (1987)). Nonhomologous plasmid-chromosome interactions are more frequent, occurring at levels $10^5$-fold (Lin et al., Proc. Natl. Acad. Sci. USA 82:1391–1395 (1985)) to $10^2$-fold (Thomas et al., Cell 44:419–428 (1986); Song et al., Proc. Natl. Acad. Sci. USA 84:6820–6824 (1987)) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transfonnant cells for homologous insertion, followed by screening individual clones (Kim et al., Nucleic Acids Res. 16:8887–8903 (1988); Kim et al., Gene 103:227–233 (1991)). Alternatively, a positive genetic selection approach has been developed in which a marker gene is constructed which will only be active if homologous insertion occurs, allowing these recombinants to be selected directly (Sedivy et al., Proc. Natl. Acad. Sci. USA 86:227–231 (1989)). One of the most powerful approaches developed for selecting homologous recombinants is the positive-negative selection (PNS) method developed for genes (such as B2) for which no direct selection of the alteration exists (Mansour et al., Nature 336:348–352: (1988); Capecchi, Science 244:1288–1292, (1989); Capecchi, Trends in Genet. 5:70–76 (1989)). The PNS method is more efficient for targeting genes which are not expressed at high levels because the marker gene has its own promoter. Nonhomologous recombinants are selected against by using the Herpes Simplex virus thymidine kinase (HSV-TK) gene and selecting against its nonhomologous insertion with the herpes drugs such as gancyclovir (GANC) or FIAU (1-(2-deoxy 2-fluoro-B-D-arabinofluranosyl)-5-iodouracil). By this counter-selection, the number of homologous recombinants in the surviving transformants can be increased.

As used herein, a "targeted gene" or "Knockout" (KO) is a DNA sequence introduced into the germline of a non-human animal by 30 way of human intervention, including but not limited to, the methods described herein. The targeted genes of the invention include DNA sequences which are designed to specifically alter cognate endogenouos alleles.

The following is presented by way of examples and is not to be construed as a limitation on the scope of the invention.

EXAMPLE 1
Preparation of the cDNA Probe by PCR:
Reverse PCR with *Theimus thermophilus* DNA polymerase (Perkin Elmer Cetus) was performed using human uterine mRNA (Clonetech). Annealing of the reverse primer and reverse transcription was done by incubating the PCR reaction minus the forward primer for 10 minutes each at room temperature, 42° C., and 60° C. PCR was performed for 35 cycles of 1 minute each at 94°, 40°, and 60° C. Two rounds of PCR were performed using degenerate primers with the restriction site adapters, NotI on the forward primer CGGCGGCCGCGCNAAYAAYTTYGAYTGG (SEQ ID NO: 3) and XhoI on the reverse primer CGCTCGAGCGYT-TYTTYTTYTCNGTYTG (SEQ ID NO: 4) The degenerate primers were designed using the hypothesized rat amino acid sequence of the rat B2 bradykinin receptor. These primers were removed using a CENTRICON 30 (AMICON, Beverly, Ma.) and a third round of PCR was performed using a second pair of nested primers (with restriction site adapters) GCGCGGCCGCAAYACNATGATHTA (SEQ ID NO: 5) and CGCTCGAGACYTCYTTRAAYTTYTTCAT (SEQ ID NO: 6). PCR products were then analyzed on a 3.5% NUSIEVE (FMC BIOPRODUCTS, Rockland, Me.) gel. A 386 bp PCR product was then subcloned into pBLUE-SCRIPT (STRATGENE, La Jolla, Ca.) and characterized by DNA sequence analysis. The probe utilized for screening was prepared by random primed synthesis (BOEHRINGER MANNHEIM BIOCHEMICALS) in the presence of [alpha-$^{32}$P]dCTP (400Ci/mmole).

EXAMPLE 2
Isolation of cDNA:
Isolation of CDNA coding for the human B2 bradykinin receptor was accomplished by first, isolating mRNA from the human cell line CCD- I 6Lu (CCL 204 obtained from the ATCC, Rockville, Md.) using the INVITROGEN FAST TRACK system. According to this procedure, CCD-16Lu cells were harvested in lysis buffer (INVITROGEN, San Diego, Ca.). The lysate was homogenized in a sterile Dounce homogenizer. The lysate was incubated at 45° C. for 1 hour and then spun at 4000 x g to remove insoluble material. The NaCi concentration was adjusted to 0.5M NaCI and a Oligo (dT) tablet was added, this mixture was then incubated by gentle rocking at room temperature for 1 hour. The Oligo (dT) was then pelleted at 4000 x g. The pellet was washed several times with binding buffer (INVITROGEN, San Diego, Ca.) and then placed into a spin-column/microcentirfuge set(INVITROGEN, San Diego, Ca.). The mRNA was eluted from the column with elution buffer (Invitrogen, San Diego, Ca.) and precipitated with sodium acetate and ethanol. CDNA was then prepared from mRNA using the BRL cDNA Synthesis System (BRL, Gaithersburg, Md.). See Gubler et al., Gene, 25, 263 (1983) as modified by BRL. BstXI adapters (INVITROGEN) were then added and the modified cDNA ligated into pcDNA II . Bacterial colonies were plated at a density of 30,000 colonies per filter and then transferred to a duplicate Durulose-UV (STRATAGENE) filters using standard techniques (Sambrook et al., supra). The probe utilized for screening was generated by random primed synthesis as described above. Duplicate filters were also hybridized with 1.5 x $10^6$ cpm/ml [$^{32}$P] labeled probe in 50% formamide hybridization solution, [5X SSC, 5X Denhart's, 100 ug/ml DNA, (SIGMA, St Louis, Mo.)] at 50° C. for 12 hours. The filters were washed at high stringency in a final wash of 0.1X SSC, 0.1% SDS at 60° C. Positive colonies were then rescreened as before. Plasmid was then isolated from second round positives and the DNA sequence was determined by double strand DNA sequencing using the Sanger method and SEQUENASE (US BIOCHEMICALS, Cleveland, Oh.).

EXAMPLE 3
Transfection and Membrane Preparation:
In order to enable expression of the cDNA that encodes for the B2 bradykinin receptor, COS-7 cells were transfected using LIPOFECTIN (BRL, Gaithersburg, Md.) with 50ug/$10^7$ cells of the B2 receptor cDNA subcloned into the eukaryotic expression vector pcDNA I-Neo (Invitrogen). Cells were then harvested after 72 hours and the membranes containing the expressed receptor protein were prepared by scraping the cells in phosphate buffered saline solution and centrifuging for ten minutes at 500x g. The cell pellet was then resuspended and homogenized with a Polytron in 20 mM N-tris(hydroxymethyl)methyl-2-aminoethane sulfonic acid (TES,pH 6.8 at room temperature) buffer containing 1 mM 1, 10 phenanthroline. The homogenate was then centrifuged for ten minutes at 500 × g. The final membrane pellet was resuspended in assay buffer (TES plus 0.1% protease free bovine serum albumin, 5 uM MK-422 (enalaprilat; Gross et al., 1981) and 140 ug/ml bacitracin using a motor-driven teflon-glass tissue homogenizer. Protein determination was performed by the method of Bradford using bovine IgG as the standard. See Bradford, M.A. Anal. Biochem. 72, 248–254 (1976).

EXAMPLE 4

Binding Assays:

Binding assays were then performed to determine receptor antagonist or agonist interaction. The assays utilized in the instant invention follow the method of Manning et al., *J. Pharmacol. Exp. Ther.*, 237, 504–512 (1986). [$^3$H]BK at various concentrations was incubated for 60 minutes at 25° C. with approximately 50ug membrane protein from COS-7 cells in a volume of 1 ml. The assay was terminated by filtration over Whatman GF/B filters presoaked for 3 hours in 0.1 % polyethyleneimine using a BRANDEL M-24 CELL HARVESTER (BRANDEL, Gaithersburg, Md.). The tubes were rinsed two times with 4 ml ice-cold 10 uM TES and the filter bound radioactivity was quantitated by liquid scintillation counting. Nonspecific binding was determined by performing incubation in the presence of 1 uM BK and generally represents less than 5% of the total binding at 100pM $^3$H]BK. Competition binding experiments, in the presence of 100pM[$^3$H]BK, were performed with varying concentrations of the test compound(s). The competition and saturation experiments were analyzed using the EBDA program of McPherson. See McPherson, G.A. *J Pharmacol. Methods* 14, 213–218 (1985).

BK-Induced Cystosolic Ca-$^{2+}$ Increases in Chinese Hamster Ovary Cells:

Preconfluent CHO cells were lifted from polystyrene culture flasks using phosphate-buffered saline containing 2mM EDTA. The cells were washed twice by centrifugation and resuspended at a density of 2×10$^6$ cells/ml in a physiological solution buffered with 10 mM HEPES, pH 7.4. The cells were incubated with 1 uM fura-2 for 40 minutes at 37° C., washed twice by centrifugation with fresh buffer and resuspended again to 2×106 cells/ml. Two ml aliquots of the suspension were then added to glass cuvettes and placed in the thermostatically controlled (37° C.) holder of a DEL-TASCAN (Photon Technology International) dual wavelength fluroimeter. Excitation was performed at 340 nm and 380 nm and emission was monitered at 510 nm. After two minutes, agonist (bradykinin or test compound) was added and the 340/380 excitation ratio was read for an additional 2 minutes. When used, antagonists were added 15 seconds prior to agonist.

Functional expression of the human B2 receptor was obtained by placing the entire B2 clone under the control of the CMV promoter (Human cytomegalo virus) in the eukaryotic expression vector, pCDNAI-Neo (Invitrogen, San Diego, Ca.). This construct was then transfected into COS-7 5 cells or CHO cells or cell lines and membranes from these cells were analyzed for expression of the B2 receptor as indicated above. Membranes prepared from transfected cells contain specific BK binding sites with a K$_D$ of 0.13 +/–0.09 nM as determined by saturation binding analysis (Data not shown). The level of expressed receptor ranges from 210 to 450 fmole/mg protein. Scatchard analysis of the saturation binding data suggested that there are two classes of BK binding sites on the membrane, a high affinity site (K$_D$=0.13nM) and a lower affinity site that is not well defined by saturation analysis (K$_D$=3nM-3uM). The lower affinity sites may arise from BK receptors which are not coupled to G-proteins. Membranes prepared from mock transfected COS-7 cells did not contain any detectable BK specific binding sites.

Competition binding studies in the COS-7 expressed receptor indicated that the cloned BK receptor binds BK analogues with the specificity of BK>lys-BK>met-lys-BK. In contrast, peptides reported to be specific for the B 1 receptor have a very low affinity for this cloned receptor. At a concentration of 10 uM, the B1 agonist Des-Arg$^9$BK and the B1 antagonist Des-Arg$^9$.LeuBK inhibited BK binding by 18% and 11% respectively. No competition for BK binding was seen with the peptides angiotensin I and II, neurotensin, oxytocin, and endothelin. These results indicated that the receptor cloned and described in the instant application has the pharmacological properties expected for a B2 bradykinin receptor.

To further illustrate this principle, the ability of the human B2 receptor to interact with well known selective B2 antagonists was analyzed (Data not shown). Competition binding studies indicated that Hoe 140 (Hock et al., Br. J. Pharmacol. 102, 774–777 (1991)), D-Arg$^0$- [Hyp$^3$,Thi$^5$,D-Tic$^7$, Oic$^8$] BK was a potent inhibitor with an IC$_{50}$ for the cloned human receptor of 65pM. [$^3$H]BK binding to the human B2 receptor was displaced by the known B2 antagonists D-Arg$^{0-[Hyp2,3}$, Thi$^{5,8}$D-Phe$^7$]BK. (IC$_{50}$=27nM) and [Thi$^{5,8}$,D-Phe$^7$]BK. (IC$_{50}$=180SOnM).

EXAMPLE 5

Preparation of murine embryonic stem cell genomic libraries

Evidence suggested that homologous genomic targeting in embryonic stem (ES) cells is strongly inhibited (>l00×) by subtle base-pair differences in their genomic DNAs (Riele et al., Proc. Natl. Acad.

Sci. USA 89:5128–5132 (1992); Deng et al., Mol. Cell. Biol. 12:3365–3371 (1992)). To circumvent this potential problem, genomic libraries were constructed from ES cells grown in the absence of feeder cell layers for the isolation of genes to be used for subsequent ES cell targeting. to the Genomic libraries were prepared from ES-J1 cells according to the in situ procedure described in (Mudgett et al., Genomics 8:623–633, (1990)). The cosmid vector sCos-1 was chosen, as it allows both the vector and the insert to be dephosphorylated. This prevents concantamer formation and generally results in genomic libraries of better quality and quantity (up to 5×10$^6$ clones per package) than is achieved with other vectors (Evans et al., Gene 79:9–20, (1989)). The DNA was transformed into and maintained in HB101 host cells.

EXAMPLE 6

Isolation of mouse bradykinin B2 receptor cosmid clones

An sCOS cosmid murine embryonic stem cell genomic library derived from mouse strain J 129 SvEv was prepared according to standard methods known in the art (Sambrook et al., supra). This library was plated on Colony/Plaque screen hybridization transfer membrane (Dupont-NEN) at a density of approximately 30,000 colonies per plate. Replicas of master plates were lysed and processed for hybridization using standard protocols (Sambrook et al., supra). The DNA was UV crosslinked to the membrane with a Stratalinker (Stratagene). The filters were incubated overnight at 42° C. with probe in 50% formamide hybridization solution, [5XSSC, 5X Denhardt's, 100 ug/ml DNA (Sigma)]. The probe, SEQ ID NO. 2, containing the coding sequence of the human B2 bradykinin receptor, was generated by random prime labelling (Boehringer Mannheim Biochemicals) in the presence of [(α-$^{32}$P]dCTP (3000 Ci/mmole). Filters were washed at a final stringency of 0.1 XSSC, 0.1%SDS at 42° C. Positives were rescreened to isolate single colonies.

EXAMPLE 7
Characterization of the mouse bradykinin B2 receptor clones

The cosmid clones for mouse bradykinin B2 were mapped with restriction endonucleases by end-ordered partial digestion (Evans et al., Gene 79:9–20, (1989)). DNA was prepared from positive colonies, digested with restriction enzymes, and Southern blot analysis was done to identify restriction fragments for subcloning. A 7.5 kB EcoR I by Hind III fragment was subcloned into pSP72 (Promega). DNA sequence analysis of a portion of the Hind III by EcoR I fragment revealed an uninterrupted open reading frame of 1101 bp:

the eukaryotic expression vector pcDNAI-Neo (Invitrogen). The PCR product begins 99 bp upstream of the initiator methionine codon and ends 49 bp downstream of the stop codon. The DNA sequence analysis using Sequenase (US Biochemical) of the subcloned PCR product confirmed that the sequence was identical to that in the original genomic fragment.

Saturation binding to whole COS cells transiently expressing the mouse $B_2$ receptor indicated a single high affinity site with a KD for [$^3$H]BK of 200 +/−30 pM and a Bmax that ranged from 650 to 1700 fmol/mg protein. The binding of BK to membranes was reduced by increasing

```
ATGTTCAACGTCACCACACAAGTCCTGCGGTCTGCTCTTAACGGA
CCCTTTCGAAAGGACAACTGCCCAGACACCGAGTGGTGGAGTTG
GCTCAATGCCATCCAGGCCCCCTTCCTCTGGGTCCTCTTCCTGCTG
GCCGCACTGGAGAACCTCTTTGTCCTCAGCGTGTTCTTCCTGCACA
AAAACAGCTGCACTGTGGCCGAGATCTACCTGGGCAACCTGGCA
GCGGCGGACCTCATCCTGGCCTGCGGGTTACCTTTCTGGGCCATC
ACCATCGCCAATAACTTTGACTGGGTGTTTGGAGAGGTGTTGTGC
CGGGTGGTGAACACCATGATCTACATGAACCTGTACAGCAGCATC
TGCTTCCTGATGCTCGTGAGTATCGACCGCTACCTGGCGCTGGTG
AAGACCATGTCCATGGGCCGGATGCGCGGGGTGCGCTGGGCCAA
ACTCTACAGCCTGGTGATCTGGGGCTGTACACTGCTTCTGAGTTC
ACCCATGTTGGTGTTCAGGACCATGAGGGAATACAGCGAAGAGG
GCCACAATGTCACCGCCTGCGTCATCGTCTACCCGTCCCGTTCCTG
GGAGGTGTTCACCAACGTGCTGCTGAACCTGGTGGGTTTCCTCCT
GCCCCTGAGCGTCATCACCTTCTGCACGGTGCGCATCTTGCAGGT
GCTGAGGAACAACGAGATGAAGAAGTTCAAGGAGGTCCAGACGG
AGAGGAAGGCCACCGTGCTAGTGCTGGCCGTCCTGGGGCTCTTTG
TGCTGTGTTGGGTGCCTTTCCAGATCAGCACCTTCCTGGACACGCT
CGTCCGGCTCGGCGTGCTGTCCGGATGCTGGGACGAGCACGCCGT
AGACGTCATCACGCAGATCAGTTCCTACGTGGCCTACAGCAACAG
CGGCCTCAACCCACTGGTGTACGTGATCGTGGGCAAGCGCTTCCG
GAAGAAGTCCCGAGAGGTGTACCGGGTGCTGTGCCAGAAAGGAG
GCTGCATGGGAGAACCCGTCCAGATGGAGAACTCCATGGGGACT
TTGAGAACCTCGATCTCCGTGGAACGGCAGATCCACAAGCTGCAG
GACTGGGCAGGGAAGAAACAGTGA (SEQ.ID.NO.:7)
```

This DNA sequence is 92% identical to the coding sequence of the rat $B_2$ bradykinin receptor and 84% identical to the human $B_2$ bradykinin receptor. The amino acid sequence deduced from this open reading frame has the characteristics of a G-protein coupled receptor; i.e. seven putative transmembrane domains connected by hydrophilic loops. Potential N-linked glycosylation sites in extracellular portions of the receptor and potential phosphorylation sites in intracellular regions that were noted in the sequence of rat and human $B_2$ bradykinin receptors are conserved in this mouse bradykinin receptor.

The coding sequence for the mouse $B_2$ bradykinin receptor lacks introns as does the human $B_2$ bradykinin receptor. However, a potential intron was found in the 5' untranslated region of the mouse gene. This result was revealed by comparison of the mouse genomic clone isolated herein with a partial mouse cDNA sequence containing 5' untranslated sequences and approximately 20% of the coding sequence of the mouse bradykinin receptor. The mouse genomic and cDNA sequences are 100% identical in the coding region, but diverge abruptly at a potential intron/exon boundary 7 bp upstream of the initiator methionine codon.

To verify the pharmacological properties of the mouse bradykinin $B_2$ receptor the coding sequence of the mouse $B_2$ bradykinin receptor was isolated by PCR (Perkin Elmer/Cetus) using a Techne thermocycler with the template being the EcoR I by Hind III genomic fragment in pSP72 and the 5' primer 5'-CCTCAAGCTTCTCCTTCTGCTATCC-3' (SEQ.ID.NO.:8) and the 3' primer 5'- AGCTCTAGAC CCACCAATCCTCACAC-3' (SEQ.ID.NO.:9). The PCR product was subcloned into the Hind III and Xba I sites of concentrations of GTP, guanosine 5'-O-(3–thiotriphosphate) or 5'guanylylimidodiphosphate. This decrease of BK binding in the presence of guanine nucleotides suggests that the mouse receptor is coupled to a G-protein in the COS-7 cells.

Competition binding experiments using 100 pM [$^3$H]BK revealed that the expressed mouse $B_2$ bradykinin receptor possessed a high (subnanomolar) affinity for the $B_2$ receptor agonists BK and kallidin. In contrast, the receptor had a very low affinity for the $B_1$ bradykinin receptor agonists, [des-Arg$^9$]-BK (IC50=6uM) and [des-Arg$^{10}$]-kallidin (IC50= 25uM). Therefore, the mouse bradykinin receptor reported here exhibited the classic pharmacological properties of a $B_2$ bradykinin receptor.

EXAMPLE 8
Construction of bradykinin $B_2$ gene targeting vectors

Figure 2:
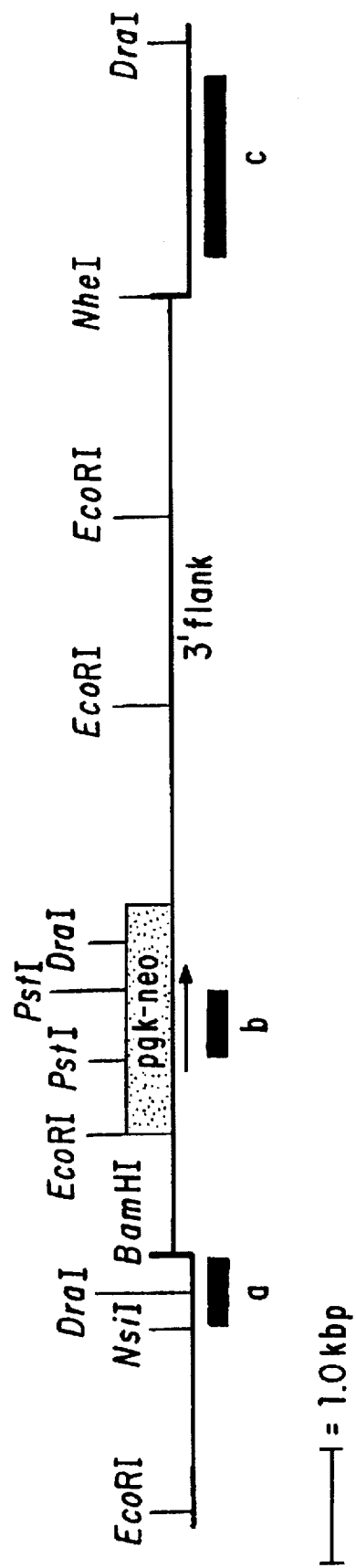
FIG. 2 is the predicted disruption of the mouse chromosomal bradykinin B2 gene by targeted gene replacement using the replacement vector.
Figure 3:
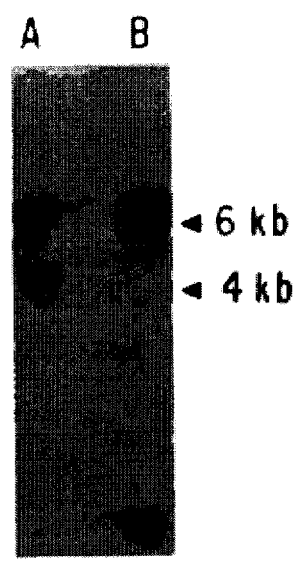
FIG. 3 is a Southern hybridization analysis of targeted embryonic stem (ES) clones having a B2 knockout. Genomic DNA was digested with EcoRI and probed with the 5' external probe. (A) DNA from a clone in which the B2 gene is disrupted; (B) DNA from a wild type clone.

From the knowledge of the genomic organization of mouse $B_2$ gene with regard to restriction sites and exons, (Example 7), gene replacement vectors for inactivating the bradykinin $B_2$ gene, and for replacing the mouse gene with the human gene, were prepared using standard cloning techniques (Sambrook et al., supra). An Sph I site was introduced into mouse $B_2$ bradykinin receptor gene by site-directed mutagenesis precisely at the codon for initiation of translation of the $B_2$ receptor. The gene replacement vector design chosen for the first gene replacement, vector pBS-KO-1, contained a 1.0 kb fragment from BamH I to the Sph I introduced by site directed mutagenesis as the short arm, a selectable neo marker inserted downstream of the short-arm by using the Eco RV site and the HindIII in pBluescript, followed by a 5.4 kb Nhe I fragment of the murine $B_2$ gene as the long arm, and a HSV-TK marker gene attached to the 5.4 kb Nhe I bradykinin $B_2$ gene fragment long arm (FIG. 2). The neo marker and the HSV-TK marker were inserted to express in the sense direction of the $B_2$ target gene. Selection against the HSV-TK gene with FIAU allowed for the enhancement of targeted recombinants as described (Mansour et al., *Nature* 336:348–352, (1988); Capecchi, *Science* 244:1288–1292, (1989); Capecchi, *Trends in Genet.* 5:70–76 (1989)). The neo and HSV-TK genes are both driven by the highly efficient mouse phosphoglycerate kinase-I (PGK-1) promoter. Use of pBS-KO-1 in gene replacement resulted in the insertion of the neo marker in the $B_2$ gene and the deletion of all of the $B_2$ coding sequences (FIG. 2). The total length of $B_2$ homology in pBS-KO-1 is 6.4 kb.

Primers were constructed and used in PCR assays to detect the inactivation of the $B_2$ gene with pBS-KO-1. Two 5' primers originated from a region 5' of the pBS-KO-1 short arm in the mouse $B_2$ promoter (5' -CCTGAAAT CACCACCTACCC-3'; SEQ. ID.NO.: 10; and 5' -CAAGCTCCTTATCCACACAGG-3' SEQ.ID.NO.:11), and the 3' primer originated from the 5' end of the neo marker gene (5'-AGGCCACTTGTGTAGCGC-3'; SEQ. ID.NO.: 12). Only $B_2$ genes having a neo marker inserted in the correct location yielded the correct PCR product. The optimal PCR conditions for use of these primers in detecting the targeted $B_2$ genes were 10 mM Tris-HCl, pH 8.3, 50 mM KCl, 3.5 mM $MgCl_2$, 0.001% (w/v) gelatin and 2.5 units AmpliTaq DNA polymerase. The reactions were run for 35 cycles of 94° C. for 30 sec, 58° C. for 45 sec, and 72° C. for 3 minutes. The detection of a 1.1 kb fragment was diagnostic of the correct homologous recombination event.

EXAMPLE 9

Targeted alteration of the bradykinin $B_2$ gene in murine ES cells The gene replacement vector used in the $B_2$ gene disruption experiments was the pBS-KO-1 vector. When this vector recombined with the wild-type $B_2$ allele to generate the $B_2$ knock-out ($B_2$ KO), the entire coding sequence for the $B_2$ receptor was deleted (FIG. 2). The mouse embryonic stem cell line AB2.1 was electroporated with Not I -linearized pBS-KO-1 in multiple experiments. All AB2.1 ES cells were cultured on SNL feeder cells as described (Robertson, in Teratocarcinomas and embryonic stem cells, IRL Press, pp. 71–112 (1987)). Electroporations were performed with $4 \times 10^6$ ES cells and 25 µg linearized pBS-KO-1 in 0.8 ml electroporation buffer (Specialty Media, Inc.) at 300v, 250 µF using a Bio-Rad Gene Pulser. ES cell transformants were selected with the antibiotic geneticin (Gibco G418: 200 µg/ml active G418), and some transformants were counter-selected with FIAU (Bristol Myers Squibb; 0.2 µM) for enhancement of homologous recombinants. Murine leukemia inhibitory factor (LIF; ESGRO, Gibco BRL, Inc.) was used at 1000 U/ml. Selection with FIAU resulted in about eleven-fold fewer background pBS-KO- 1 transformants, thereby enhancing the isolation of targeted transformants. G418–and FIAU-resistant ES clones were isolated by picking and growing individual colonies, and their genomic DNAs were prepared from AB2.1 5 KO-I-transformants as described (Laird et al., *Nucleic Acids Res.* 19:4293 (1991).

To confirm the targeted disruption of the mouse B2 allele in single ES cell lines, their genomic DNAs were digested with restriction endonucleases, transferred to Amersham Hybond-N membranes, and genomic Southern hybridizations were performed according to established protocals (Sambrook, et al. supra). The ES cell genomic DNAs were hybridized with the neo gene, as well as 5' and 3' flanking unique sequence DNA probes. The 5' unique probe resides (5' -3' ) from the Nsi I to the BamH I site, and the 3' unique probe resides (5' -3' ) from the Nhe I to the EcoR I site in sCos (FIG. 2). Digestion with EcoR I and and hybridization of genomic DNA from a $B_2$ targeted ES cell line to the Nsi I/BamH I probe yielded two hybridizing fragments, one wild-type 6 kb allele and one targeted 4 kb allele. Several cell lines contained both hybridizing fragments. Further Southern hybridization analysis using the Nhe I/EcoRI probe hybridized to Dra I digested genomic DNA yielded two hybridizing fragments, one wild type 9 kb allele and one targeted 7.5 kb allele. The neo gene probe confirmed that these clones contain the targeted (knocked-out) B2 allele, and that the regions flanking the B2 target were unaltered.

To replace the mouse B2 bradykinin receptor with the human B2 bradykinin receptor an Sph I restriction site was introduced into the mouse B2 receptor gene as described above for the knockout construct. Site directed mutagenesis was utilized to place an Sph I site in an analogous position in the coding sequence for the human B2 receptor. The human B2 receptor coding sequence had previously been cloned into the mammalian expression vector pcDNA1-Neo (Invitrogen) and expressed in mammalian cells. The restriction enzymes Not I and ApaL I were used to excise the human B2 receptor coding sequence from pcDNAI-Neo along with DNA sequences that are important for the stability of mRNA transcripts (an intron and a polyadenylation site). This fragment was placed downstream of the short arm of the knockout construct. The subsequent steps in the construction of the replacement vector i.e. the addition of the neo marker gene, the long arm, and the HSV-TK marker gene were identical to the knockout construct. PCR analysis was not utilized to screen for ES with the targeted replacement of the mouse B2 receptor with the human B2 receptor.

Figure 6:
FIG. 6 is a Southern hybridization analysis of targeted embryonic stem (ES) clones having a human B2 gene. Genomic DNA was digested with Dra I and hybridized with the 3' external probe. Lanes (A) wild type AB2.1 DNA; (B) DNA from an ES cell clone with a disruption of the mouse B2 receptor; (C and D) DNA from ES cell clones containing the replacement of the mouse B2 receptor coding sequence with the human B2 receptor coding sequence.
Figure 7:
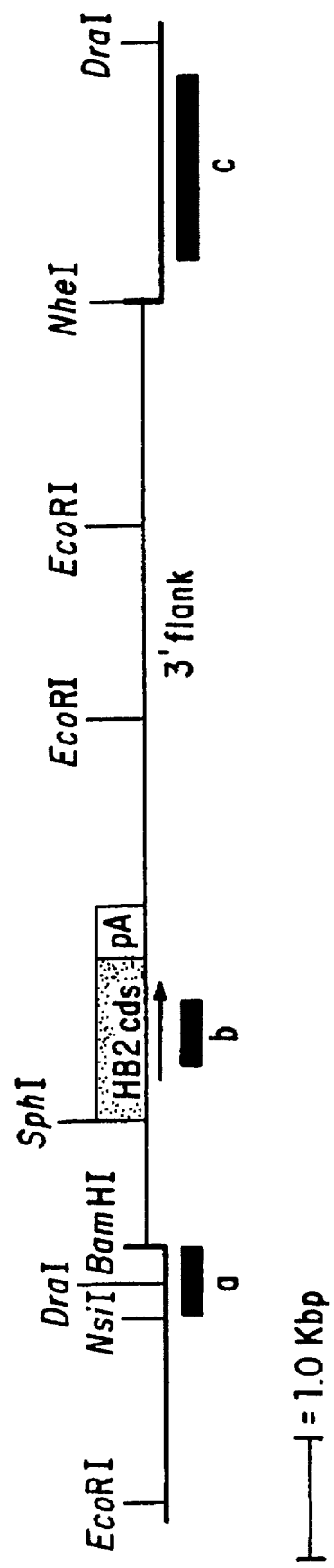
FIG. 7 is the predicted replacement of the mouse chromosomal bradykinin B2 gene with the human bradykinin B2 by targeted gene replacement using the replacement vector.

To confirm the targeted replacement of the mouse B2 allele with the human B2 coding sequence in single ES cell lines, their genomic DNAs are digested with restriction endonucleases, transfened to Amersham Hybond-N membranes, and genomic Southern hybridizations are performed according to established protocols (Sambrook, et al. supra). The ES cell genomic DNAs are hybridized with 5' and 3' flanking unique sequence DNA probes. The 5' unique probe resides (5' -3' ) from the Nsi I to the BamH I site, and the 3' unique probe resides (5' -3' ) from the Nhe I to the EcoR I site in sCos. Digestion with Sph I and and hybridization of genomic DNA from a B2 targeted ES cell line to the Nsi I/BamH I probe yields hybridizing fragments having the targeted 3.5 kb allele. Cell lines containing both hybridizing fragments are identified. Further Southern hybridization analysis using the Nhe I/EcoRl probe hybridized to Dra I digested genomic DNA yields two hybridizing fragments, one wild type 9 kb allele and one targeted 7.5 kb allele (FIG. 6). Southern hybridization analysis using an 800 ) bp human B2 gene probe hybridizes to EcoR I digested genomic DNA yielding two hybridizing fragments, one wild type allele of 6 kb and one targeted allele of 5 kb. These results will confirm that these clones contain the targeted replacement at the murine B2 allele with the human B2 coding sequence and that the regions flanking the B2 target are unaltered (FIG. 7).

EXAMPLE 10

Injection of altered B2 clones into donor blastocysts

All B2-targeted AB2.1 cell lines were characterized by PCR and Southern hybridization analysis to confirm that B2 was disrupted or replaced with the human DNA. The cell lines were grown in culture and characterized. Targeted cell lines which grew normally and did not contain an abnormal proportion of differentiated cells (Robertson, supra) were then separated from their feeder cells by treating the cell culture with trypsin, allowing the feeder cell to attach for 30-45 minutes, and removing the unattached ES cells. The ES cells were injected into recipient blastocysts. Two B2 targeted ES clones, KO-5 and KO-24, were injected into C57B1/6J recepient blastocysts in separate experiments usning techniques described previously (Bradley, A. "Production and analysis of chimeric mice. In: Teratocarcinomas and Embryonic Stem Cells: A Practical Approach", E.J. Robertson (ed.) Oxford:IRL Press, (1987), pp 113-151). The injected C57B1/6J recipient blastocysts were reimplanted into the uterii of day 3 pseudopregnant Tac:SW(fBR) mice and allowed to develop to term. Progeny were screened initially by coat color chimerisim, the agouti color (which is the ES cell background strain) being an indicator of ES cell chimerism.

Injection of the B2 targeted line KO-24 yielded 13 progeny mice, of which 5 (one female and four males) were coat color chimerics. As the ES cell line AB2.1 is homozygous for the agouti (A) coat color gene, penetrance of ES cells into the injected (black coat color) C57B1/6 blastocyst gives rise to chimeric coat color mice.

EXAMPLE 11
Breeding chimeric mice

The 4 chimeric coat color male mice from the first injection were bred to wild-type C57B1/6 (black coated) and 129/J (agouti coated) female mice. Some of the progeny from the chimera X C57B1/6 cross were expected to be agouti if the chimeric male had ES cell genetic material incorporated into its germline (agouti is dominant to black coat color). The chimera X 129/J cross yield would only agouti mice. These crosses were performed to test for the transfer of ES cell genetic information, including the disrupted or replaced B2 allele, to its offspring.

Figure 4:
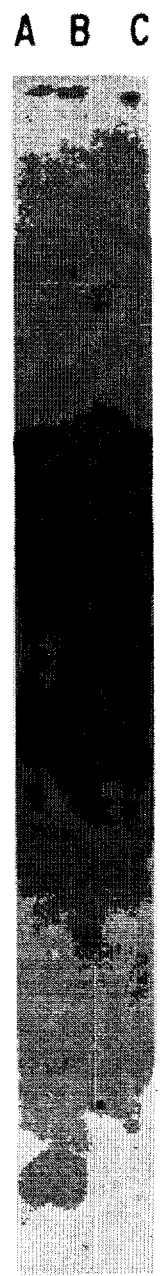
FIG. 4 is a Southern hybridization analysis of heterozygous (F1) transgenic mice having a B2 knockout. Genomic DNA was extracted from a tail biopsy, digested with Dra I, and probed with the 3' external probe. Lane (A) DNA from a wild type mouse, (B and C) DNA from heterozygous mice.

To determine the B2 genotypes, genomic DNA was purified from about 1 cm of tail from each mouse after weaning. The genomic DNA was isolated as described (Laird et al., supra), followed by phenol and phenol:chloroform extractions and ethanol precipitation. Southern hybridization analysis (as described in Example 9) were used to identify offspring which contained the disrupted B2 allele or the human gene. These transgenic offspring were heterozygous for the B2 disruption or the human gene. Both transgenic heterozygous and nontransgenic mouse (tail) genomic DNAs were digested with Dra I, and hybridized with 3' flanking DNA probes to confirm the transgenic B2 structure (FIG. 4). Southern hybridization analysis confirmed that the structure of the altered bradykinin B2 allele was identical to that predicted, and previously characterized in the B2 targeted ES clones.

Figure 5:
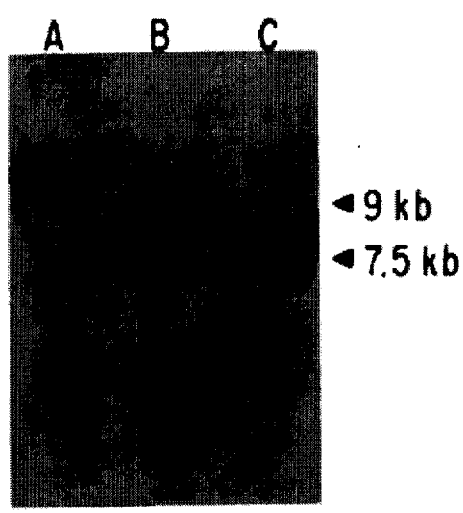
FIG. 5 is a Southern hybridization analysis of homozygous (F2) transgenic mice having a B2 knockout. Southern analysis of genomic DNA digested with Dra I and hybridized with the 3'external probe from F2 (het. x het. crosses) yielded the following patterns: Lane (A) a wild type mouse; (B) a heterozygous mouse; (C) a homozygous knockout mouse.

EXAMPLE 12
Breeding heterozygous mice and generation of homozygous bradvkinin B2 deficient mice Male and female transgenic mice, each of which contained one copy of the altered bradykinin B2 allele (heterozygous mice), were mated with each other to generate mice in which both copies of the bradykinin B2 gene were the targeted, altered transgenic B2 gene. It was predicted that one fourth of the mouse embryos would be homozygous for the altered bradykinin B2 gene. Surviving offspring were genotyped by Southern hybridization as described above (FIG. 5). It was determined that 33% of the 110 offspring mice were homozygous B2-/-, 17% were wild-type B2+/+, and 50% were heterozygous B2-/+. These numbers indicate that there was no significant decrease in the number of bradykinin B2 deficient or the human B2 replacement transgenic mice which survived past weaning. The homozygous B2-/- mice were designated B2r-.

EXAMPLE 13
Characterization of homozygous bradvkinin B2 deficient mice

Significant differences in gross morphology or motor activity between the bradykinin B2 deficient mice and the wild-type or heterozygous mice were not observed.

---

What is claimed is:

1. A transgenic mouse harboring a homozygous null mutation in its endogenous bradykinin B2 receptor gene wherein said null mutation has been introduced into said mouse or an ancestor of said mouse via homologous recombination in embryonic stem cells, and further wherein said mouse does not express a functional mouse bradykinin B2 receptor.

2. The transgenic mouse of claim 1, wherein said mouse is fertile and transmits said null mutation to its offspring.

3. The transgenic mouse of claim 1, wherein said null mutation has been introduced into an ancestor of said mouse at an embryonic stage following microinjection of embryonic stem cells into a mouse blastocyst.

4. The transgenic mouse of claim 1, wherein said null mutation has been introduced into an ancestor of said mouse at an embryonic stage following coincubation of embryonic stem cells with a fertilized egg or a morula.

5. The mouse of claim 1, which is designated B2r.

6. A transgenic mouse whose somatic and germ cells contain a gene encoding a human bradykinin B2 receptor wherein the endogenous mouse bradykinin B2 receptor gene is replaced by said human gene in said mouse or an ancestor of said mouse following homologous recombination in embryonic stem cells, and further wherein said transgenic mouse does not express an endogenous mouse bradykinin B2 receptor and does express a human bradykinin B2 receptor.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3680 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AAAATGGACT  TGAGATGGGT  CACTACTCCA  GCTTTGTCTG  CTTTGTTCTC  CCCAGTCTGG      60

AGGTTTTTAA  AAAATCTCCT  TTGGGCCCAA  TCCAGGATTC  CTGATGATGG  TGATGGAGGT     120

GAGGGTGGTG  AGGGTGGTGA  TGGTGGTGAT  GGTGGTGATG  GTGGTGATGG  TGCTGTTGAT     180

AGTGATGATG  ATGGTGGTAA  GGGAGGAGGG  ATGCTGGGTC  TGTGCCCTCC  TGAAATCACC     240

ACCTACCCAG  GACTCATCAC  AGAGGAGTCC  ATGACTGTTA  AGAGAAAAAC  AAGCTCCTTA     300
```

-continued

```
TCCACACAGG AGCTACAGGG GCTCTAGATA CCTCAGGATC CAAACCATGT CACCATGAGT    360
CACAGGCCCC GGCCTGGCTC TAGGGTAGCG CCAGCCCAGC AGACACTCCG GGGCTCTTCC    420
TGAGAAACCT CAGGATGCTG AGCAGAGCCT TCTCATCATT CTGCCTAGTG CCTCCTTTCC    480
CCTGCCCCGC AGTGGAAGGG TCCTCCCATC CCCCACTCTG CAGGTGACTA GTCACACGTG    540
CCCTGGGTGT GCTTTAGGCT TTTTAGTGCA TCTTTATAAT CATGTTTCGA TATTATTCCC    600
ATCTTTACTG GTTAGGGGTC CAAAAACATT AAGCAACTTA CCAAGGCCAA ACGGTGACCA    660
GGACTCGGCC CCAGGGGACC AAGCCAAAGT CTCGCCTTTC CTCTTTCCAG GCAACCTTGG    720
CTCACCTTCT GTGCTTTGCT GCCAGTGGGC ACAGGCACAA GGTTCTCCCT CTGCTAGAAG    780
ACACAGATTG TCATGGAGGT GGCTGTGCTC TGGGGGGCCA GACTGCAGTC TCTCCACCTG    840
GCATGGCATC GCTGATCTGG TCTAATTTAT GGCTCACCTG TGACCCCACT CTGAGGAGCT    900
GATGGGTCAC GGTCCACAGG GGAGAGGCAT GAGAAGGCAG CGAGCACATC TCATAGTGGA    960
GGCTTCAAAG GGCTCCAGGT GTGGCATTCA CGACCATTGG AGTAGCCAGG GAAGGATTCT   1020
TACAGAGTTC AGACCAAGAA ATATCATGTC CCTTTGGTCC CAGGAAGATC TCTCAAAGGA   1080
CTGGAGAGTC CAAGTCCCCT AGTGCTGTCC ACAGACCGGA GTCCACCAC CTCCCCACAC   1140
CCCACTGCCG CCGGGAGTCA TCAGCTGAAC AATAGACTTT CTGGTCCACC TGTCCTGTGC   1200
TCCTCCCTGG CCCTCCACCT CCTCCTTCTG CTATCCCGTT TTCTCTTCCC CTCCCCTCCC   1260
CCTCCTTGTG ACCTGAGGAT ACGACTGTCT CTTCTCTACT TTCTTTCAGC ATCGAAATGT   1320
TCAACGTCAC CACACAAGTC CTCGGGTCTG CTCTTAACGG GACCCTTTCG AAGGACAACT   1380
GCCCAGACAC CGAGTGGTGG AGTTGGCTCA ATGCCATCCA GGCCCCTTC CTCTGGGTCC   1440
TCTTCCTGCT GGCCGCACTG GAGAACCTCT TTGTCCTCAG CGTGTTCTTC CTGCACAAAA   1500
ACAGCTGCAC TGTGGCCGAG ATCTACCTGG GCAACCTGGC AGCGGCGGAC CTCATCCTGG   1560
CCTGCGGGTT ACCTTTCTGG GCCATCACCA TCGCCAATAA CTTTGACTGG GTGTTTGGAG   1620
AGGTGTTGTG CCGGGTGGTG AACACCATGA TCTACATGAA CCTGTACAGC AGCATCTGCT   1680
TCCTGATGCT CGTGAGTATC GACCGCTACC TGGCGCTGGT GAAGACCATG TCCATGGGCC   1740
GGATGCGCGG GGTGCGCTGG GCCAAACTCT ACAGCCTGGT GATCTGGGC TGTACACTGC   1800
TTCTGAGTTC ACCCATGTTG GTGTTCAGGA CCATGAGGGA ATACAGCGAA GAGGGCCACA   1860
ATGTCACCGC CTGCGTCATC GTCTACCCGT CCCGTTCCTG GAGGTGTTC ACCAACGTGC   1920
TGCTGAACCT GGTGGGTTTC CTCCTGCCCC TGAGCGTCAT CACCTTCTGC ACGGTGCGCA   1980
TCTTGCAGGT GCTGAGGAAC AACGAGATGA AGAAGTTCAA GGAGGTCCAG ACGGAGAGGA   2040
AGGCCACCGT GCTAGTGCTG GCCGTCCTGG GGCTCTTTGT GCTGTGTTGG GTGCCTTTCC   2100
AGATCAGCAC CTTCCTGGAC ACGCTGCTGC GCCTCGGCGT GCTGTCCGGA TGCTGGGACG   2160
AGCACGCCGT AGACGTCATC ACGCAGATCA GTTCCTACGT GGCCTACAGC AACAGCGGCC   2220
TCAACCCACT GGTGTACGTG ATCGTGGGCA AGCGCTTCCG GAAGAAGTCC GAGAGGGTGT   2280
ACCGGGTGCT GTGCCAGAAA GGAGGCTGCA TGGAGAACC CGTCCAGATG GAGAACTCCA   2340
TGGGGACTTT GAGAACCTCG ATCTCCGTGG AACGGCAGAT CCACAAGCTG CAGGACTGGG   2400
CAGGGAAGAA ACAGTGAACA GAAGCCACCA GGCAGGACTA CTGCCAAGTG TGTGAGGATT   2460
GGTGGGACCG GAGCTCCTCA GCCTGGGTTC AGAAGGAGCT TGAAGCATCC TAGGCAGCCC   2520
CAGGGAATCA GGCAGGTGAC TCCAGCCCTG TCTCATGGCA TAAGCATGCT GTGGGGAATG   2580
GGTACCCTGG GGCACAGCAG GGTCATTCTT ACTGACTGAC GCTCTAATTC TCCATGAGTG   2640
GAGGGGTCAT GGGTATGGGT GGGAGTGACA GAGCTTCCTT CCCTTTTGGG GAAGGACAGA   2700
```

-continued

| | | | | | |
|---|---|---|---|---|---|
|TCTCCTGCCA|GCTTTGGCCC|TGTGGCTACA|TGCACAGTAG|GCATGGCCGC|CTCATTTCCC|2760|
|AGTTTCAAGG|GTATAAGATT|TATTGGTCTT|CTGAAGGTTA|AATTCTATGG|TAAGAGCCCA|2820|
|GGGACTGGGT|TCTGTGGCTC|CTTTCACCTG|TAGACAAGGT|GGACAGCACA|AAAGAAGAGC|2880|
|CCCCAAAGCA|TTTATGGAGC|ACTTGTTGAA|TACACACCGT|TATACACTGA|GGGCAAGAGG|2940|
|AAAGAACTGC|ATAGTTTAAT|GTCTTATAGG|AGCCCTGACA|TTAGCGGAGA|ATACCGAGAA|3000|
|GGCTGCTGCT|GGTGTGCCAA|AGCAAGGAAC|TGTGGGAGAC|GGGAGAGTAC|AGGGCCCAGG|3060|
|CTAGCCAGTA|ACCCCGAACA|CGGTAGCCTC|ATCCCTGCCT|CTGCTTCTTC|GGTTGTAATC|3120|
|TGAGGGTGTC|CTGGGCTTTG|AAAGTGGGGT|GTTATATGGC|TGTGAGGCAT|TGTGACCCAC|3180|
|ACCACCACAT|GCAGACGCAT|TGGGACTCTT|GGCACAGAGA|AAGCCACTCA|GGCTGAAGAG|3240|
|CTACTCTGTG|GGGACACTTA|GTATTGGAAG|GCCCAGTACC|TGCCTGCAGT|GTCTGCGGCC|3300|
|CTCAGTCCCC|TCTATCTTTC|CCTCCTAGTA|TTTCACCCCT|ATGCACACAA|AGCACAAAGC|3360|
|ATTTGCTCCA|CAGGAAGGGC|AAGGGCGGGA|GACAGCGAGT|GTTTGTTTTG|CAGGGAAACA|3420|
|AAGAAAAAGG|AATTCATCGA|TGATATCAGA|TCTGCCGGTC|TCCCTATAGT|GAGTCGTATT|3480|
|AATTTCGATA|AGCCAGGTTA|ACTGCATTAA|TGAATCGGCC|AACGCGCGGG|GAGAGGCGGT|3540|
|TTGCGTATTG|GGCGCTCTTC|CGCTTCCTCG|CTCACTGACT|CGCTGCGCTC|GGTCGTTCGG|3600|
|CTGCGGCAGC|GTATCAGCTC|ACTCAAGCGG|TAATACGTAT|CACAGAATCA|GGGATACGCA|3660|
|GGAAGACATG|TGAGAAAGGC| | | | |3680|

( 2 ) INFORMATION FOR SEQ ID NO:2:

( i ) SEQUENCE CHARACTERISTICS:
        ( A ) LENGTH: 1378 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
|CTCCGAGGAG|GGGTGGGGAC|GGTCCTGACG|GTGGGACAT|CAGGCTGCCC|CGCAGTACCA|60|
|GGGAGCGACT|TGAAGTGCCC|ATGCCGCTTG|CTCCGGGAGA|AGCCCAGGTG|TGGCCTCACT|120|
|CACATCCCAC|TCTGAGTCCA|AATGTTCTCT|CCCTGGAAGA|TATCAATGTT|TCTGTCTGTT|180|
|CGTGAGGACT|CCGTGCCCAC|CACGGCCTCT|TTCAGCGCCG|ACATGCTCAA|TGTCACCTTG|240|
|CAAGGGCCCA|CTCTTAACGG|GACCTTTGCC|CAGAGCAAAT|GCCCCAAGT|GGAGTGGCTG|300|
|GGCTGGCTCA|ACACCATCCA|GCCCCCCTTC|CTCTGGGTGC|TGTTCGTGCT|GGCCACCCTA|360|
|GAGAACATCT|TTGTCCTCAG|CGTCTTCTGC|CTGCACAAGA|GCAGCTGCAC|GGTGGCAGAG|420|
|ATCTACCTGG|GGAACCTGGC|CGCAGCAGAC|CTGATCCTGG|CCTGCGGGCT|GCCCTTCTGG|480|
|GCCATCACCA|TCTCCAACAA|CTTCGACTGG|CTCTTTGGGG|AGACGCTCTG|CCGCGTGGTG|540|
|AATGCCATTA|TCTCCATGAA|CCTGTACAGC|AGCATCTGTT|TCCTGATGCT|GGTGAGCATC|600|
|GACCGCTACC|TGGCCCTGGT|GAAAACCATG|TCCATGGGCC|GGATGCGCGG|CGTGCGCTGG|660|
|GCCAAGCTCT|ACAGCTTGGT|GATCTGGGGG|TGTACGCTGC|TCCTGAGCTC|ACCCATGCTG|720|
|GTGTTCCGGA|CCATGAAGGA|GTACAGCGAT|GAGGGCCACA|ACGTCACCGC|TTGTGTCATC|780|
|AGCTACCCAT|CCCTCATCTG|GGAAGTGTTC|ACCAACATGC|TCCTGAATGT|CGTGGGCTTC|840|
|CTGCTGCCCC|TGAGTGTCAT|CACCTTCTGC|ACGATGCAGA|TCATGCAGGT|GCTGCGGAAC|900|
|AACGAGATGC|AGAAGTTCAA|GGAGATCCAG|ACGGAGAGGA|GGGCCACGGT|GCTAGTCCTG|960|
|GTTGTGCTGC|TGCTATTCAT|CATCTGCTGG|CTGCCCTTCC|AGATCAGCAC|CTTCCTGGAT|1020|

```
ACGCTGCATC  GCCTCGGCAT  CCTCTCCAGC  TGCCAGGACG  AGCGCATCAT  CGATGTAATC   1080

ACACAGATCG  CCTCCTTCAT  GGCCTACAGC  AACAGCTGCC  TCAACCCACT  GGTGTACGTG   1140

ATCGTGGGCA  AGCGCTTCCG  AAAGAAGTCT  TGGGAGGTGT  ACCAGGGAGT  GTGCCAGAAA   1200

GGGGGCTGCA  GGTCAGAACC  CATTCAGATG  GAGAACTCCA  TGGGCACACT  GCGGACCTCC   1260

ATCTCCGTGG  AACGCCAGAT  TCACAAACTG  CAGGACTGGG  CAGGGAGCAG  ACAGTGAGCA   1320

AACGCCAGCA  GGGCTGCTGT  GAATTGTGT   AAGGATTGAG  GGACAGTTGC  TTTTCAGG    1378
```

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
CGGCGGCCGC  GCNAAYAAYT  TYGAYTGG                                          28
```

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CGCTCGAGCG  YTTYTTYTTY  TCNGTYTG                                          28
```

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
GCGCGGCCGCA  AYACNATGAT  HTA                                              24
```

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
CGCTCGAGAC  YTCYTTRAAY  TTYTTCAT                                          28
```

( 2 ) INFORMATION FOR SEQ ID NO:7:

( i ) SEQUENCE CHARACTERISTICS:
        ( A ) LENGTH: 1101 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:7:

| | | | | | |
|---|---|---|---|---|---|
| ATGTTCAACG | TCACCACACA | AGTCCTGCGG | TCTGCTCTTA | ACGGACCCTT | TCGAAAGGAC | 60
| AACTGCCCAG | ACACCGAGTG | GTGGAGTTGG | CTCAATGCCA | TCCAGGCCCC | CTTCCTCTGG | 120
| GTCCTCTTCC | TGCTGGCCGC | ACTGGAGAAC | CTCTTTGTCC | TCAGCGTGTT | CTTCCTGCAC | 180
| AAAACAGCT | GCACTGTGGC | CGAGATCTAC | CTGGGCAACC | TGGCAGCGGC | GGACCTCATC | 240
| CTGGCCTGCG | GGTTACCTTT | CTGGGCCATC | ACCATCGCCA | ATAACTTTGA | CTGGGTGTTT | 300
| GGAGAGGTGT | TGTGCCGGGT | GGTGAACACC | ATGATCTACA | TGAACCTGTA | CAGCAGCATC | 360
| TGCTTCCTGA | TGCTCGTGAG | TATCGACCGC | TACCTGGCGC | TGGTGAAGAC | CATGTCCATG | 420
| GGCCGGATGC | GCGGGGTGCG | CTGGGCCAAA | CTCTACAGCC | TGGTGATCTG | GGGCTGTACA | 480
| CTGCTTCTGA | GTTCACCCAT | GTTGGTGTTC | AGGACCATGA | GGGAATACAG | CGAAGAGGGC | 540
| CACAATGTCA | CCGCCTGCGT | CATCGTCTAC | CCGTCCGTT | CTGGGAGGT | GTTCACCAAC | 600
| GTGCTGCTGA | ACCTGGTGGG | TTTCCTCCTG | CCCCTGAGCG | TCATCACCTT | CTGCACGGTG | 660
| CGCATCTTGC | AGGTGCTGAG | GAACAACGAG | ATGAAGAAGT | TCAAGGAGGT | CCAGACGGAG | 720
| AGGAAGGCCA | CCGTGCTAGT | GCTGGCCGTC | CTGGGGCTCT | TTGTGCTGTG | TTGGGTGCCT | 780
| TTCCAGATCA | GCACCTTCCT | GGACACGCTC | GTCCGGCTCG | GCGTGCTGTC | CGGATGCTGG | 840
| GACGAGCACG | CCGTAGACGT | CATCACGCAG | ATCAGTTCCT | ACGTGGCCTA | CAGCAACAGC | 900
| GGCCTCAACC | CACTGGTGTA | CGTGATCGTG | GGCAAGCGCT | TCCGGAAGAA | GTCCCGAGAG | 960
| GTGTACCGGG | TGCTGTGCCA | GAAAGGAGGC | TGCATGGGAG | AACCCGTCCA | GATGGAGAAC | 1020
| TCCATGGGGA | CTTTGAGAAC | CTCGATCTCC | GTGGAACGGC | AGATCCACAA | GCTGCAGGAC | 1080
| TGGGCAGGGA | AGAAACAGTG | A | | | | 1101

( 2 ) INFORMATION FOR SEQ ID NO:8:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

CCTCAAGCTT CTCCTTCTGC TATCC    25

( 2 ) INFORMATION FOR SEQ ID NO:9:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

AGCTCTAGAC CCACCAATCC TCACAC    26

( 2 ) INFORMATION FOR SEQ ID NO:10:

( i ) SEQUENCE CHARACTERISTICS:
( A ) LENGTH: 20 base pairs
( B ) TYPE: nucleic acid

```
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:10:

CCTGAAATCA CCACCTACCC                                                    2 0

( 2 ) INFORMATION FOR SEQ ID NO:11:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:11:

CAAGCTCCTT ATCCACACAG G                                                  2 1

( 2 ) INFORMATION FOR SEQ ID NO:12:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:12:

AGGCCACTTG TGTAGCGC                                                      1 8
```